US008507000B2

(12) United States Patent
Mulye

(10) Patent No.: US 8,507,000 B2
(45) Date of Patent: Aug. 13, 2013

(54) CONTROLLED RELEASE FORMULATION OF ERYTHROMYCIN DERIVATIVES

(75) Inventor: Nirmal Mulye, Kendall Park, NJ (US)

(73) Assignee: Nostrum Pharmaceuticals, Inc., Kendall Park, NJ (US)

( * ) Notice: Subject to any disclaimer, the term of this patent is extended or adjusted under 35 U.S.C. 154(b) by 0 days.

(21) Appl. No.: 10/555,849

(22) PCT Filed: May 6, 2004

(86) PCT No.: PCT/US2004/014031
§ 371 (c)(1),
(2), (4) Date: Sep. 28, 2006

(87) PCT Pub. No.: WO2004/100880
PCT Pub. Date: Nov. 25, 2004

(65) Prior Publication Data
US 2007/0053979 A1    Mar. 8, 2007

Related U.S. Application Data

(60) Provisional application No. 60/468,204, filed on May 6, 2003.

(51) Int. Cl.
*A61K 9/22* (2006.01)
*A61K 31/70* (2006.01)

(52) U.S. Cl.
USPC ............................................ 424/468; 514/29

(58) Field of Classification Search
None
See application file for complete search history.

(56) References Cited

U.S. PATENT DOCUMENTS

| 3,931,404 | A | | 1/1976 | Fülberth et al. | |
|---|---|---|---|---|---|
| 4,588,712 | A | | 5/1986 | Toscano | |
| 5,141,926 | A | | 8/1992 | Weber et al. | |
| 5,605,889 | A | * | 2/1997 | Curatolo et al. | 514/29 |
| 5,705,190 | A | | 1/1998 | Broad et al. | |
| 6,010,718 | A | * | 1/2000 | Al-Razzak et al. | 424/464 |
| 6,068,859 | A | * | 5/2000 | Curatolo et al. | 424/490 |
| 6,248,363 | B1 | * | 6/2001 | Patel et al. | 424/497 |
| 6,642,276 | B2 | * | 11/2003 | Wadhwa | 514/781 |
| 2002/0136766 | A1 | | 9/2002 | Rudnic et al. | |
| 2003/0077324 | A1 | | 4/2003 | Mulye | |

FOREIGN PATENT DOCUMENTS

| JP | 49-86526 | | 8/1974 |
|---|---|---|---|
| JP | 60-208995 | A | 10/1985 |
| JP | 2-502720 | A | 8/1990 |
| JP | 10-87656 | A | 4/1998 |
| JP | 2002-173428 | A | 6/2002 |
| WO | 88/07366 | A1 | 10/1988 |

OTHER PUBLICATIONS

English language translation of Japanese Office Action issued in Patent Application No. 2006-532793 mailed Sep. 14, 2010.

* cited by examiner

*Primary Examiner* — Elli Peselev
(74) *Attorney, Agent, or Firm* — Scully, Scott, Murphy & Presser, P.C.

(57) ABSTRACT

The present invention is directed to a controlled release formulation in tablet form comprising a pharmaceutically effective amount of an erythromycin derivative and a lubricating effective amount of a lubricant in the absence of material selected from the group consisting of alginic acid or salts thereof or hydrophilic sustained release polymers in amounts effective to retard the release of the erythromycin derivatives in the pharmaceutical composition. It is also directed to a method for facilitating the release of erythromycin derivative from a pharmaceutical composition comprising a therapeutically effective amount of a lubricating effective amount of a lubricant said method comprising adding to said composition an release promoter in tablet disintegrating effective amounts to facilitate the release of the erythromycin derivative from the tablet.

47 Claims, No Drawings

CONTROLLED RELEASE FORMULATION OF ERYTHROMYCIN DERIVATIVES

RELATED APPLICATION

The present application is claiming benefit of PCT application PCT/US2004/014031 under 35 USC §371 filed on May 6, 2005, which in turn claims the benefit of U.S. Provisional application U.S. Ser. No. 60/468,204 filed on May 6, 2003.

FIELD OF THE INVENTION

The present invention relates to a controlled release pharmaceutical composition comprising an erythromycin derivative, and more particularly clarithromycin.

BACKGROUND OF THE INVENTION

Erythromycin and its derivatives are known for their antibacterial activity against a number of organisms. An example of an erythromycin derivative is 6-O-methoxyerythromycin A, better known as clarithromycin.

The erythromycin compositions have been typically administered at least two to three times daily as immediate release compositions. Clarithromycin, for example, has to be administered at least twice daily for optimal effects.

Sustained release formulations, however, are preferred. Well-absorbed oral sustained or slow release therapeutic drug dosage forms have inherent advantages over conventional, immediate release dosage forms. A less frequent dosing of a medicament, as is required by a sustained release dosage form, increases the resultant patient regime compliance, provides a more sustained drug blood level response, and effects therapeutic action with less ingestion of a drug, thereby mitigating many potential side effects. By providing a slow and steady release of a medicament over time, absorbed drug concentration spikes are mitigated or eliminated by effecting a smoother and more sustained blood level response.

Even in a sustained release formulation, the daily dose of the drug is 1000 mg. The daily dose of 1000 mg is presently administered to patients in two tablets. The 500 mg tablet currently marketed is quite large with a tablet weight of about 1000 mg. Thus, there is a need in the marketplace to make a smaller tablet containing 500 mg clarithromycin and/or to make a 1000 mg tablet which is not unacceptably large.

Various sustained release formulations containing clarithromycin have been described. For example, U.S. Pat. No. 5,705,190 to Broad, et al. describes controlled release formulations for sparingly soluble basic drugs, such as erythromycin derivatives, including clarithromycin, comprising the drug in association with a water soluble alginate salt, a complex salt of alginic acid, and an organic carboxylic acid to facilitate dissolution of the drug at higher pH. However, the total tablet weight of each tablet containing 500 mg drug as described in the examples is more than 900 mg, as substantial amounts of polymers are required for controlling the rate of drug release. Thus, a single tablet containing 1,000 mg drug made in accordance with the teachings therein would be at least 1,800 mg. This would be unacceptably large for human consumption.

U.S. Pat. No. 6,010,718 to Al-Razzak, et al. describes an extended release pharmaceutical dosage for erythromycin derivatives, such as clarithromycin using from about 5 to about 50% by weight of a pharmaceutically acceptable polymer, such as a water soluble polymer, for example, polyvinylpyrrolidine, hydroxypropylcellulose, hydroxypropylmethyl cellulose, methyl cellulose, vinyl acetate/crotonic acid copolymers, methacrylic acid copolymers, maleic anhydride/methyl vinyl ether copolymers, and derivatives and mixtures thereof. However, the total weight of each tablet containing 500 mg drug, as described in the examples, is close to 1000 mg. Once again a single tablet would be unacceptably large at 2000 mg, thus necessitating the administration of two tablets of 500 mg strength, each for delivering the daily dose of 100 mg clarithromycin.

These prior art formulations require a high concentration of polymer, such as 10-30% by weight to be used to control the release of the drug. Not only is this a large amount of polymer, but also this tends to make the oral dosage form quite large. Additionally, sticking and picking of tablets are common problems with this drug. Moreover, the tableting characteristics of these formulations are quite poor, and additional excipients are added to improve the tableting characteristics.

However, the present inventor has found another method of preparing a sustained release formulation in which sustained release hydrophilic polymers or alginic acid or salts thereof are not required. Moreover, the present inventor has found a means of preparing a sustained release formulation comprising erythromycin derivatives such as clarithromycin, in which the drug is present in at least 75% by weight of the oral dosage form.

More specifically, the present inventor has found that erythromycin derivatives, such as clarithromycin can form a tablet matrix by itself in combination with a lubricant when placed in aqueous medium and can achieve slow release without the aid of controlled release polymers, especially hydrophilic controlled release polymers or alginic acid or salts thereof. The matrix thus formed does not disintegrate, and is quite stable in aqueous solution, and the inventor has found that it releases the drug by erosion. Using the methodology of the present invention, a sustained release formulation in tablet form can be prepared containing a high concentration of an erythromycin derivative, such as clarithromycin. Thus, for example, a tablet with a concentration of an erythromycin derivative, such as clarithromycin as high as 90% by weight or higher can be prepared.

SUMMARY OF THE INVENTION

Accordingly, the present invention is directed to a controlled release solid pharmaceutical composition in tablet form adapted for oral administration comprising a pharmaceutically effective amount of an erythromycin derivative and a lubricating effective amount of a lubricant in the absence of alginic acid or salt thereof or pharmaceutically acceptable hydrophilic sustained release polymers in amounts effective to retard the release of the erythromycin derivative therefrom. In another embodiment, the present invention is directed to a controlled release solid pharmaceutical composition in tablet form adapted for oral administration comprising a pharmaceutically effective amount of an erythromycin derivative, a lubricant in lubricating effective amounts and a disintegrating effective amount of a release promoter, in the absence of a material selected from alginic acid or salt thereof and pharmaceutically acceptable hydrophilic sustained release polymer present in a concentration effective to retard the release of the erythromycin derivative therefrom. The present invention is also directed to a method for facilitating the release of erythromycin derivative from a pharmaceutical composition comprising a therapeutically effective amount of a lubricating effective amount of a lubricant said method comprising adding to said composition an release promoter in tablet disintegrating effective amounts to facilitate the release of the erythromycin derivative from the tablet.

DETAILED DESCRIPTION OF THE INVENTION

One embodiment of the present invention is directed to a controlled release formulation of an erythromycin derivative in tablet form for oral administration comprising a pharmaceutically effective amount of said erythromycin derivative and a lubricating effective amount of a lubricant in the absence of a material selected from the group consisting of alginic acid or salts thereof and hydrophilic sustained release polymers that are present in amounts effective to retard the release of the erythromycin derivatives from the pharmaceutical composition.

As described hereinbelow, the present invention does not exclude alginic acid or salts thereof or hydrophilic sustained release polymers. On the contrary, as described hereinbelow, the pharmaceutical composition of the present invention includes alginic acid or salts thereof and sustained release hydrophilic polymers as long as they are not present and do not function to retard the release of the erythromycin derivative from the pharmaceutical composition. However, if either functions to retard the release of the erythromycin derivatives, they are excluded from the composition of the present invention.

As used herein, the term "pharmaceutical" refers to a medicinally administered composition or compositions as a whole.

"Erythromycin derivatives", as used herein refers to an erythromycin having no substituents thereon or having conventional substituent groups in organic synthesis, in place of a hydrogen atom of the hydroxy groups and/or a methyl group of the 3'-dimethylamino group, which is prepared according to the conventional manner. An example thereof is clarithromycin.

"Pharmaceutically acceptable", as used herein refers to those compounds, which are, within the scope of sound medical judgement, suitable for use in contact with tissues of humans and other mammals without under toxicity, irritation, allergic response, and the like in keeping with a reasonable benefit/risk ratio and effective for their intended use in therapy and prophylaxis of anti-microbial infections.

The preferred patient to which the drug is being administered is a mammal, such as a horse, cow, pig, dog, cat, monkey, mice, rat, human, and the like. The preferred patient and mammal is a human.

The phrase "unit dosage form", as employed herein, refers to physically discrete units suitable as unitary dosages to human subjects and other mammals, said unit containing a predetermined quantity of the erythromycin derivative, such as clarithromycin, calculated to produce the desired medical effect, such as anti-bacterial effect, in association with other ingredients of the formulation disclosed herein. The unit dosage form referred to herein is a solid unit dosage form and most preferably a tablet.

The phrase "direct tableting" and like terms, as used herein, signify that the composition can be formed into a tablet using well known tableting apparatus and processes without the need for addition of any additional material to the composition.

As used herein, the term "kp" means kilopounds, a well known unit of force for expressing hardness or crushing strength of pharmaceutical tablets when such hardness is determined.

The percentage of ingredients (a pharmaceutical, polymer, excipients and other ingredients) required in the formulation of the present invention are calculated on a dry weight basis without reference to any water or other components present.

The sustained release formulation of the present invention has an excellent drug profile and is stable with a long shelf life. Moreover, in the sustained release formulation of the present invention, the rate of release of the active agent from the tablet is consistent and uniform among tablets prepared at different times and in different manufacturing batches. The bio-availability characteristics of the tablet prepared in accordance with the procedure herein are substantially uniform among different batches.

In accordance with the present invention, the pharmaceutical composition contains a pharmaceutically active compound. The pharmaceutically active compound is an erythromycin derivative. Preferably, the erythromycin derivatives is 6-O-methoxy erythromycin A, also known as clarithromycin. The erythromycin derivative is present in therapeutically effective amounts. Preferably, the drug content in the pharmaceutical composition of the present invention ranges from about 40% by weight of the pharmaceutical composition e.g., tablet to about 99% by weight and more preferably from about 50% to about 95% by weight of the pharmaceutical composition and more preferably from about 50% by weight to about 90% by weight, and most preferably from about 50 to about 85% by weight of the tablet.

The other essential ingredient of the present invention is the lubricant.

"Lubricant", as used herein, refers to a material which can reduce the friction between the die walls and the punch faces which occurs during the compression and ejection of a tablet. The lubricant prevents sticking of the tablet material to the punch faces and the die walls. As used herein, the term "lubricant" includes anti-adherents.

Tablet sticking during formation of a tablet and/or ejection may pose serious production problems such as reduced efficiency, irregularly formed tablets and non-uniform distribution of the medicament in the formulation. To avoid this problem, the present invention contemplates utilizing a lubricating effective amount of the lubricant. Preferably, the lubricant is present in amounts ranging from about 0.1% to about 10% by weight and more preferably from about 1% to about 10% by weight and even more preferably from about 0.5% to about 5% by weight and most preferably from about 10% to about 3% by weight and even most preferably from about 2% to about 5% of the pharmaceutical composition, e.g., tablet. The present inventor has found that lubricants in lubricating effective amounts also act as releasing agents in the pharmaceutical composition of the present invention and help facilitate the release of the erythromycin derivative therefrom. Examples of lubricants include stearate salts, e.g., alkaline earth and transition metal salts, such as calcium, magnesium and zinc stearates; stearic acid, polyethylene oxide; talc; hydrogenated vegetable oil; and vegetable oil derivatives, and the like. In addition, the pharmaceutical composition, e.g., tablet, may contain a combination of more than one type of lubricant. Other lubricants that also can be used include silica, silicones, high molecular weight polyalkylene glycol, monoesters of propylene glycol, and saturated fatty acids containing about 8-22 carbon atoms and preferably 16-20 carbon atoms. The preferred lubricants are the stearate salts, especially magnesium and calcium stearate and stearic acid, glyceryl behenate, hydrogenated vegetable oil, hydrophilic formed silica, sodium stearyl fumarate and the like.

Hydrophilic lubricants, such as glyceryl behenate, stearic acid, hydrogenated vegetable oil can also act as a formulation aid by helping to form a non-disintegrating tablet. If the tablet contains a high concentration of a hydrophilic ingredient, such as 40-60% by weight, the hydrophilic lubricants can help prevent premature disintegration of the matrix. Hydrophobic lubricants, however tend to slow down the release of the erythromycin derivatives from the pharmaceutical composition.

On the other hand, hydrophilic lubricant, such as hydrophilic fumed silica, salts of stearic acid, sodium stearyl fumarate and the like enhance the release of the erythromycin derivatives from the pharmaceutical composition. The present inventor has found that the erythromycin, such as clarithromycin can form a stable tablet matrix with only lubricant present.

Such a formulation when administered to patients or placed in an aqueous system can slowly release the drug, erythromycin derivative. However, in many situations, the release may be too slow. As a result, additional components may be added to the pharmaceutical composition to accelerate the release. One such additional component is an release promoter, also known as a disintegrent.

In a preferred embodiment, the pharmaceutical composition also contains a release promoter. The term "release promoter" refers to a material, which promotes erosion of the drug matrix and helps regulate the release of the drug. Release promoters are a term of art known to one of ordinary skill in the art. Examples of erosion promoting agents are vegetable oil, starch, such as corn starch, modified starch and starch derivatives, cellulose derivatives and modified cellulose or derivatives, e.g., methylcellulose, sodium carboxymethyl cellulose, alginic acid and alginate, bentonite, veagum, polyvinylpyrrolidone, cross-linked polyvinylpyrrolidine, ion-exchange resins and gums, such as agar guar, and the like. In addition, they may include commonly used excipients, such as hydrophilic diluents or fillers, such as microcrystalline cellulose, silicified microcrystalline cellulose, maltodextrin lactose, starch, compressible sugar and the like. Other release promoters include pharmaceutically acceptable water soluble organic acids, especially dicarboxylic acids containing 2-6 carbon atoms, normally used as excipients. Examples include acetic acid, acrylic acid, adipic acid, alginic acid, alkane sulfonic acids, ascorbic acids, benzoic acid, butyric acid, carbonic acid, cinnamic acid, formic acid, fumaric acid, gluconic acid, isoascorbic acid, lactic acid, maleic acid, methane sulfonic acid, oxalic acid, propionic acid, p-toluene sulfonic acid, succinic acid, and tartaric acid, and the like.

Hydrophilic surfactants can also act as release promoters. A suitable hydrophilic surfactant will generally have an HLB value of at least 10. As is well known, surfactants must necessarily include polar or charged hydrophilic moieties as well as non-polar lipophilic moieties, that is, a surfactant must be amphiphilic. An empirical parameter commonly used to characterize the relative hydrophilicity and hydrophobicity of non-ionic amphiphilic compounds is the hydrophilic lipophilic balance ("HLB value"). Surfactants with lower HLB values are more lipophilic and have greater solubility in aqueous solutions. Hydrophilic surfactants are generally considered to be those compounds having an HLB value greater then about 10, as well as an ionic, cationic or zwitterionic compounds for which an HLB scale is not generally applicable.

The Hydrophilic surfactants used in the present invention may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptins, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof.

Within the aforementioned group, preferred ionic surfactants include, by way of example: the ionized from a surfactant selected from the group consisting of: lecithins, lysolecithin, phospholipids, lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof.

More preferred ionic surfactants are the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof. The preferred ionic surfactant is sodium lauryl sulfate.

Preferred hydrophilic non-ionic surfactants include alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof.

More preferably, the hydrophilic non-ionic surfactant is selected from the group consisting of polyethylene glycol sorbitan fatty acid esters and hydrophilic transesterification products of a polyol with at least one member of the group consisting of triglycerides, vegetable oils, and hydrogenated vegetable oils. The polyol is preferably glycerol, ethylene glycol, polyethylene glycol, sorbitol, propylene glycol, pentaerythritol, or a saccharide.

Examples of hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 40, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Among these preferred non-ionic surfactants, more preferred are PEG-20 laurate, PEG-20 oleate, PEG-35 castor oil, PEG-40 palm kernel oil, PEG-40 hydrogenated castor oil, PEG-60 corn oil, PEG-25 glyceryl trioleate, polyglyceryl-10 laurate, PEG-6 caprate/caprylate glycerides, PEG-8 caprate/caprylate glycerides, PEG-30 cholesterol, polysorbate 20, polysorbate 80, POE-9 lauryl ether, POE-23 lauryl ether, POE-10 oleyl ether, PEG-24 cholesterol, sucrose monostearate, sucrose monolaurate and poloxamers. Most preferred are PEG-35 castor oil, PEG-40 hydrogenated castor oil, PEG-60 corn oil, PEG-25 glyceryl trioleate. PEG-6 caprate/caprylate glycerides, PEG-8 caprate/caprylate glycerides, polysorbate 20, polysorbate 40, polysorbate 80, tocopheryl PEG-1000 succinate, PEG-24 cholesterol, and hydrophilic poloxamers.

The release promoter, if present, is present in the pharmaceutical composition in disintegrating effective amounts. It is present in an amount sufficient to regulate the release of the tablet, that is, in an amount sufficient to facilitate the release of the erythromycin derivative in a controlled manner. Preferably, it is present in an amount ranging form about 0.1% by weight to about 60% by weight, and more preferably from about 10% to about 60% by weight and even more preferably from about 15% to about 45% by weight. However, the preferred amounts of the release promoter present is dependent upon the type of release promoter.

For example, if the release promoter is an organic acid, it is preferably present in an amount ranging from about 0.1 to about 10% by weight of the pharmaceutical composition and even more preferably from about 0.5 to about 5% and more preferably, from about 1% to about 5% and most preferably from about 1% to about 3% by weight.

If the release promoter is a water soluble surfactant, it is present in an amount ranging from about 0.01 to about 5% by weight and more preferably from about 0.1% to about 3% by weight of the pharmaceutical composition.

On the other hand, if the release promoter is a hydrophilic diluent or filler, as described hereinabove, it is preferably present in an amount ranging from about 10% top about 60% by weight of the pharmaceutical composition and more preferably is about 15% to about 45% by weight of the pharmaceutical composition.

It is to be noted that the alginic acid or salts thereof and the hydrophilic polymers, if present in the present composition serve the exact opposite function than that normally expected.

As described in the prior art, many of these serve to retard or slow down the release of the medicament from the drug. Even in the clarithromycin formulations described in the Background of the Invention, they tend to help retard the release of the clarithromycin from the pharmaceutical composition. However, in the present invention, in the concentrations used, they help facilitate the release of the erythromycin derivative from the pharmaceutical composition. Thus, if present, they are present in amounts sufficient to facilitate the release.

As one skilled in the art is well aware, the maximum amount will vary depending upon the identity and amount of other ingredients present in the pharmaceutical composition. Thus, depending on the formulations a particular amount of hydrophilic polymer or alginic acid or salt thereof may facilitate the release of the medicament, while in another formulation, the same amount may act to retard the release of the medicament. Nevertheless, for a given formulation, they act as release promoters and facilitate the release of the erythromycin derivative from the pharmaceutical composition when present in lower amounts, and act to retard the release thereof when present in the higher amounts. One of ordinary skill in the art can determine the appropriate amount of these polymers and of alginic acid or salts thereof to add to the formulation therein to act as release promoters.

Another optional ingredient that may be present are binders. These are used to improve the tableting characteristics. Examples of suitable binder materials include, but are not limited to starch, pregelatinized starch, gelatin, sugars (including sucrose, glucose, dextrose, lactose and sorbitol), polyethylene glycol, waxes, natural and synthetic gums, such as acacia, tragacanth, sodium alginate, cellulose especially hydrophilic cellulose, such as hydroxypropyl methyl cellulose, polyvinylpyrolidoxy, hydroxypropyl cellulose or polyethylene glucose, and the like, synthetic polymers such as acrylic acid and methacrylic acid copolymers, methyl methacrylate compolymers, amino alkyl methacrylate copolymers, polyacrylic acid/polymethacrylic copolymers, polyacrylic acid, and polymethylacrylic acid. If present, the preferred polymeric binder is PVP or HPMC polyethylene glycol or hydroxypropyl cellulose. The most preferred polymeric binder is PVP or HPMC.

If present, the binders are present in amounts effective to facilitate the tableting characteristics, i.e., amounts effective for the various components in the pharmaceutical compositions to be compressed into a tablet. If a binder is present, it is preferably present in low concentrations, preferably less than about 10% by weight of the pharmaceutical composition. More preferably, if present it is present in amounts ranging from about 1% to about 10% by weight of the tablet, more preferably from about 2% to about 6% by weight and even more preferably from about 2% to about 5% by weight of the pharmaceutical composition.

Moreover, the hydrophilic polymeric binders at these concentrations can act as release promoters. Again, if it acts as an release promoter, it is present in amounts effective to act as an release promoter and facilitate pharmaceutical composition. If it acts as an release promoter, then it is present in amounts effective to enhance tableting and to facilitate the release of the erythromycin derivatives form the pharmaceutical compositions, which amounts are preferably in the ranges indicated hereinabove.

The present inventor has found that the same hydrophilic sustained release polymers can elicit opposite effects, depending upon its concentration present in the pharmaceutical composition. On the one hand, these hydrophilic polymers can act as sustained release polymers. In order to control the release of a medicament, the hydrophilic polymer must be able to hydrate or swell so that it can form a firm gel before the dosage form disintegrates. But, in addition, the polymer has to be able to firm a form gel which will resist dissolution as well as disintegration. In order to effect this second objective, it must form a continuous gel network around the medicament in the pharmaceutical composition. This second objective can only be accomplished if the hydrophilic sustained release polymer is present in high enough concentration to form such a gel network. If, on the other hand, the hydrophilic sustained release polymer is not present in sufficiently high concentrations, a continuous gel network cannot be formed and thus cannot prevent the dosage form from disintegration. It can only swell, thereby promoting the disintegration, i.e. facilitating the release of the medicament. Thus, at the higher concentration, a sustained release polymer will retard the release of the medicament, while at the lower concentrations it will facilitate the release of the medicament.

The pharmaceutical composition may additionally contain a hydrophobic water insoluble material such as wax, as a sustained release agent. Such sustained release material is described in United States Patent Application No. 20030077324, the contents which are incorporated by reference. Examples include glyceryl behenate, hydrogenated vegetable oil, stearic acid, glyceryl monostearate, glycerpalmito stearate, cetyl alcohol and the like. If present, they are present in the amounts described therein.

Other optional ingredients that are also typically used in pharmaceuticals may also be present, such as coloring agents, preservatives (e.g., methyl parabens), fillers, diluents artificial sweeteners, flavorants, anti-oxidants, and the like. Artificial sweeteners include, but are not limited to, saccharin sodium, aspartame, dipotassium glycyrrhizinate, stevia, thaumatin and the like. Flavorants include, but are not limited to, lemon, lime, orange and menthol. The colorants include, but are not limited to, various food colors, e.g., FD&C colors, such as FD&C Yellow No. 6, FD&C Red No. 2, FD&C Blue No. 2, food lakes and the like. Examples of anti-oxidants include ascorbic acid, sodium metabisulphite and the like. These optional ingredients, if present, preferably are present in amounts ranging from about 0.1% to about 5% by weight of the tablet and most preferably less than about 3% (w/w) of the tablet. Examples of fillers include, but not limited to, dicalcium phosphate and calcium sulfate, and the like.

The formulations of the present invention are preferably uncoated, but may be coated if desired with one of the many readily available coating systems. Nevertheless, it is to be understood that the components described hereinabove, i.e., erythromycin derivative, lubricant, release promoter, if present, binder, if present, and the optional ingredients described hereinabove are present in the core. The coating, if present surrounds the core, the coating may either be non-functional or functional.

The coating may mask the taste of the pharmaceutical composition of the present invention. Alternatively, coatings may be used to make the unit dosage form of the pharmaceutical composition of the present invention, e.g., tablet, easier to swallow and, in some cases, improve the appearance of the dosage form. The pharmaceutical compositions, e.g., tablet, can be sugar coated; they are sugar coated according to the procedures well known in the art. Alternatively, the unit dosage forms of the pharmaceutical composition of the present invention, e.g., tablets, can be coated with any one of numerous polymeric film coating agents frequently employed by formulation chemists. Representative examples of such film coating agents include hydroxypropyl methylcellulose, carboxymethylcellulose, hydroxypropylcellulose, methyl cellulose, ethyl cellulose, acrylic resins, polyvinyl povidone (PVP), polyvinyl diethylaminoacetate, cellulose acetate phthalate, polyvinyl acetate phthalate, acrylic latex emulsions, ethyl cellulose latex emulsions, gums, starch and the like. The coating may be used to prevent the initial burst of release. A combination of water soluble or water insoluble polymers may be used. If the coating is HPMC, it is preferred that it is of low molecular weight, i.e., the CPS ranges from about 5 to about 15.

The coat may contain the optional ingredients described hereinabove. The coat can also help the matrix to maintain its integrity. If present, the coat may be present in amounts ranging from about 0.5 to about 10% by weight, more preferably from about 1 to about 10% by weight and even more preferably from about 1% to about 6% by weight, and especially more preferably from about 2% to about 5% and more preferably about 2 to about 4% by weight of the pharmaceutical composition.

In another embodiment the pharmaceutical composition in tablet form additionally comprises maltodextrin in combination with a cellulose derivative selected from the group consisting of microcrystalline cellulose and especially silicified microcrystalline cellulose.

The oral dosage form of the present invention can be manufactured by methods familiar to one of ordinary skill in the art. The preferred methods for preparing the tablets of the present invention are direct compression and wet granulation.

In direct compression, the erythromycin derivative, lubricant and the other components present are milled to the desired particle size using milling apparatus known to one of ordinary skill in the art. Preferably, the components are milled by passing them through a t mesh filter such as in a mechanical vibrosifter. The various milled components are mixed together until homogenous using a blender that is typically used in the pharmaceutical arts, such as Hobart mixer, V-blender, planetary mixer, Twin-shell blender, and the like. It is preferred that the ingredients are blended together at about ambient temperatures, no additional heating is required, although slight modification of temperature therefrom could be utilized, for example, at temperatures ranging from about 10° C. to about 45° C. In an alternative direct compression method, the lubricant is not initially milled or mixed with the erythromycin derivative or other components, but is added to the mixture towards the end of the mixing process. Again, the components are mixed together until homogenous. Whichever dry method is used the mixing is effected under effective conditions and for sufficient time to ensure uniform mixing of the ingredients.

An alternative procedure for preparing the formulation of the present invention is by the wet granulation process in which all of the components i.e. medicament, lubricant, release promoter, if present, binder, if present and any additional excipients and other optional ingredient(s), are milled to the desired size using the appropriate mesh in a milling apparatus known to one of ordinary skill in the art, such as a mechanical vibrosifter. They are then mixed with a sufficient amount of a granulating solvent until homogenous to form a substantially uniform blend in a suitable blender, such as a planetary mixer, Hobart mixer, V blender and the like. The granulating vehicle is one that is inert to the components and has a low boiling point, i.e., preferably less than about 120° C. It is preferably a solvent such as an alcohol containing 1-4 carbon atoms, e.g., isopropyl alcohol or ethanol or water or acetone and the like. The selection and use of granulating solvent are both known to one of ordinary skill in the art. The ingredients are blended together at effective temperatures and for sufficient time to ensure uniform mixing of ingredients. It is preferred that the mixing occurs at room temperature, although slight modifications of temperature therefrom could be utilized. For example, the blending may be effected at temperature ranging from about 10° C. to about 45° C. The ingredients in the formulation are mixed together using techniques well known in the pharmaceutical arts and are intimately intermixed until the mixture is homogenous with respect to the drug.

The substantially uniformly blended mixture may next optionally be milled, e.g., passed through a screen, sieve, etc. to reduce the size of the particles thereof. The screen or sieve, is preferably 6-14 mesh, and more preferably about 12 mesh.

Next, the blend is dried. In this step, the solvent is removed from the blend by physical means known to the skilled artisan, e.g., by evaporation or filtration. The drying is performed at temperatures effective to dry the moist granules, e.g., about 50 to about 80° C. For example, if isopropyl alcohol is used as the granulating agent, it is preferably affected at temperatures of about 50° to about 80° C. and more preferably, 60-70° C. If water is used as the wet granulation process, the granules are dried at about 70° C. to about 80° C. The resulting granules are again milled, e.g., passed through a screen or sieve to further reduce the size of the particles to the desired size. The lubricant is added, and the granules are mixed to provide a uniform and homogenous blend, and then the resulting mixture is compressed to form a tablet. In a preferred variation, the blend can be simultaneously granulated in the granulation vehicle and dried, such as by using a fluid bed granulation process. In a variation of preparing the drug formulation, all of the above steps are repeated, except that the mixing is initially performed in the absence of a lubricant. When the mixture is homogeneous with respect to the drug, in the last mixing, just before compression, then the lubricant is added and the mixing is continued until the lubricant is substantially evenly dispersed or homogenous in the mixture. Then the mixing is terminated, and the mixture is immediately thereafter compressed into a tablet, as described hereinabove.

Whichever method is used the ingredients in the formulation are preferably mixed together such as, e.g., in a large batch, using techniques well known in the pharmaceutical arts and are intimately intermixed until the mixture is homogenous with respect to the drug.

The term "homogenous" with respect to the drug is used to denote that the various components are substantially uniform throughout the invention, i.e., a substantially homogeneous blend is formed.

When the mixture is homogeneous, a unit dosage amount of the mixture is made into a solid dosage form, such as a tablet. The tablet preferably contains 100 mg to 1500 mg inclusive of erythromycin derivative and more preferably 500 mg to 1000 mg inclusive of erythromycin derivative.

In making a tablet, the homogenous mixture is compressed into a tablet form using a tablet machine typically utilized in the pharmaceutical arts. More specifically, the mixture is fed to the die of a tablet press and sufficient pressure is applied to form a solid tablet. Such pressure can vary, and typically ranges from about 1,000 psi to about 6,000 psi and preferably about 2,000 psi force. The solid formulation according to the present invention is compressed to a sufficient hardness to prevent the premature ingress of the aqueous medium into the tablet. Preferably, the formulation is compressed into a tablet form which is of the order of 12-40 Kp and more preferably 15-30 Kp as determined by a Schleuniger hardness test.

When the mixture from either procedure is homogeneous with respect to the drug, a unit dosage form of the mixture is prepared and then compacted, as described hereinabove.

After the tablet is formed, the tablet may be coated with materials normally used in pharmaceuticals, if desired. If coated, the coating is prepared by techniques known in the art.

As a result of the process described herein, a tablet product is obtained which has the desired hardness and friability typically found for pharmaceutical tablets. The hardness is preferably 12-40 Kp and more preferably 15-30 Kp. In addition, the tablet has an excellent drug release profile. More specifically, it has a predetermined controlled and sustained action release pattern so that the drug is available over a period of at least 2 hours and up to 12 hours or event up to 36 hours or longer, depending upon the precise tablet size, hardness and the particular carrier composition and the needs of the patient. Furthermore, the release profile of each formulation is substantially uniform. Finally, the tablets prepared in accordance with the present invention are hard and dense, have low friability and provide controlled and sustained release over an extended period.

Moreover, the process described herein is capable of producing pharmaceutical compositions in tablet form wherein the erythromycin derivatives, such as clarithromycin is present in amounts greater than about 75% by weight of the tablet. For example, attention is directed to Examples 1, 3, 4, 5, 6, 13B, 14A, 14B and 15A and 15B hereinbelow. Moreover, as shown each produce an excellent release profile. However, patient compliance with the dosage regiment by patients is easier since the full daily allotment of the erythromycin can be administered by ingesting one tablet instead of two.

Further, the present inventor has also shown that using the process described herein, tablets can be prepared which are as large as the sustained release formulation of the prior art, but yet do not contain the sustained release hydrophilic polymers or alginic acid or salts thereof. Moreover, they exhibit and excellent drug release profiles.

Unless indicated to the contrary, all percentages are weight percentages relative to the pharmaceutical composition in solid oral dosage form.

Furthermore, the terms "sustained release" and "controlled release" are being used interchangeably.

As used herein, the singular shall refer to the plural and vice versa.

The following non-limiting examples further illustrate the present invention.

Example 1

| Ingredient | Quantity per tablet, mg | % content |
|---|---|---|
| Clarithromycin | 500 | 96.2 |
| Mg Stearate | 10 | 1.9 |
| Hydrophilic fumed silica | 10 | 1.9 |
| Tablet weight | 520 | |

Tablets were manufactured by the direct compression method by milling the clarithromycin and excipients separately using a screen of 40 mesh in a mechanical vibrosifter. The milled components are combined and mixed in a binder at room temperature until uniform mixing of ingredients is obtained. The lubricant is next added at the end of the mixing steps; and the mixture, including the lubricant is compressed into a tablet using a tablet press.

The dissolution profile was determined using a USP apparatus in an aqueous medium. More specifically, the clarithromycin was dissolved in 500 mL of a 0.1 M sodium acetate buffer. The apparatus used was a USP Type 2, Paddle at a speed of 50 rpm.

The amount of clarithromycin dissolved in the 0.1 M sodium acetate buffer is determined at specific time intervals of 1, 3, 5, 7, 9 and 12 hours using a Shimadzer HPLC system. The results are tabulated hereinbelow.

| Time (Hours) | Cumulative % Released |
| --- | --- |
| 1 | 13 |
| 3 | 24 |
| 5 | 32 |
| 7 | 39 |
| 9 | 45 |
| 12 | 55 |

Example 2

| Ingredient | Quantity per tablet, mg | % content |
| --- | --- | --- |
| Clarithromycin | 500 | 50 |
| Maltodextrin M 180 | 465 | 47.4 |
| Mg Stearate | 15 | 1.5 |
| Tablet weight | 980 | |

Tablets were manufactured by the direct compression method in accordance with the procedure of Example 1. The dissolution profile was determined using the procedure of Example 1. The results are as follows:

| Time (Hours) | Cumulative % Released |
| --- | --- |
| 1 | 17 |
| 3 | 35 |
| 5 | 50 |
| 7 | 64 |
| 9 | 81 |
| 12 | 98 |

Example 3

| Ingredient | Quantity per tablet, mg | % content |
| --- | --- | --- |
| Clarithromycin | 1000 | 83.3 |
| Silicified Microcrystalline cellulose | 182 | 15.2 |
| Mg Stearate | 18 | 1.5 |
| Tablet weight | 1200 | |

Tablets were manufactured by the direct compression method, in accordance with the procedure of Example 1. The dissolution was determined using the procedure of Example 1 except that the clarithromycin was dissolved in 1000 ml of 0.1 M sodium acetate buffer. The results are as follows:

| Time (Hours) | Cumulative % Released |
| --- | --- |
| 1 | 15 |
| 3 | 50 |
| 5 | 75 |
| 7 | 92 |
| 9 | 94 |
| 12 | 93 |

Example 4

| Ingredient | Quantity per tablet, mg | % content |
| --- | --- | --- |
| Clarithromycin | 1000 | 83.3 |
| Silicified Microcrystalline cellulose | 182 | 15.2 |
| Mg Stearate | 18 | 1.5 |
| Tablet weight | 1200 | |
| Coating, Opadry 29019 (low molecular weight HPMC) | 36 | 3 |

Tablets were manufactured by the direct compression method, as described in Example 1. The tablets were coated using perforated pan coating. The dissolution profile was determined using the procedure described in Example 3. The results are as follows:

| Time (Hours) | Cumulative % Released |
| --- | --- |
| 1 | 7 |
| 3 | 39 |
| 5 | 61 |
| 7 | 77 |
| 9 | 85 |
| 12 | 90 |

Example 5

| Ingredient | Quantity per tablet, mg | % content |
| --- | --- | --- |
| Clarithromycin | 1000 | 83.3 |
| Maltodextrin M 180 | 182 | 15.2 |
| Mg Stearate | 18 | 1.5 |
| Tablet weight | 1200 | |

Tablets were manufactured by the direct compression method, as described in Example 1. The dissolution profile was determined using the procedure described in Example 3. The results are as follows:

| Time (Hours) | Cumulative % Released |
| --- | --- |
| 1 | 19 |
| 3 | 32 |
| 5 | 38 |
| 7 | 42 |
| 9 | 45 |
| 12 | 52 |

Example 6

| Ingredient | Quantity per tablet, mg | % content |
| --- | --- | --- |
| Clarithromycin | 1000 | 90.9 |
| Silicified Microcrystalline cellulose | 41.8 | 3.8 |
| Maltodextrin M 180 | 41.8 | 3.8 |

| Ingredient | Quantity per tablet, mg | % content |
|---|---|---|
| Mg Stearate | 16.5 | 1.5 |
| Tablet weight | 1100 | |

Tablets were manufactured by the direct compression method, as described in Example 1. The dissolution profile was determined using the procedure described in Example 3. The results are as follows:

| Time (Hours) | Cumulative % Released |
|---|---|
| 1 | 9 |
| 3 | 20 |
| 5 | 26 |
| 7 | 31 |

Example 7

| Ingredient | Quantity per tablet, mg | % content |
|---|---|---|
| Clarithromycin | 500 | 51.02 |
| Silicified Microcrystalline cellulose | 232.5 | 23.7 |
| Maltodextrin M 180 | 232.5 | 23.7 |
| Mg Stearate | 15 | 1.6 |
| Tablet weight | 980 | |

Tablets were manufactured by the direct compression method as described in Example 1. The dissolution profile was determined using the procedure described in Example 1. The results are as follows:

| Time (Hours) | Cumulative % Released |
|---|---|
| 1 | 19 |
| 3 | 54 |
| 5 | 69 |
| 7 | 74 |
| 9 | 96 |
| 12 | 99 |

Example 8

| Ingredient | Quantity per tablet, mg | % content |
|---|---|---|
| Clarithromycin | 500 | 51.0 |
| Silicified Microcrystalline cellulose | 220 | 22.5 |
| Maltodextrin M 180 | 220 | 22.5 |
| Glyceryl behenate | 25 | 2.5 |
| Mg Stearate | 15 | 1.5 |
| Tablet weight | 980 | |

Tablets were manufactured by the direct compression method, as described in Example 1. The dissolution profile was determined using the procedure described in Example 1. The results are as follows:

| Time (Hours) | Cumulative % Released |
|---|---|
| 1 | 14 |
| 3 | 36 |
| 5 | 64 |
| 7 | 85 |
| 9 | 94 |
| 12 | 97 |

Example 9

| Ingredient | Quantity per tablet, mg | % content |
|---|---|---|
| Clarithromycin | 500 | 51.0 |
| Silicified Microcrystalline cellulose | 220 | 22.5 |
| Maltodextrin M 180 | 220 | 22.5 |
| Glyceryl behenate | 25 | 2.5 |
| Mg Stearate | 15 | 1.5 |
| Tablet weight | 980 | |
| Coating: Opadry YS-1-7006 clear | 29.4 | 3 |

Tablets were manufactured by the direct compression method, as described in Example 1. The dissolution profile was determined using the procedure described in Example 1. The results are as follows:

| Time (Hours) | Cumulative % Released |
|---|---|
| 1 | 11 |
| 3 | 28 |
| 5 | 50 |
| 7 | 72 |
| 9 | 88 |
| 12 | 93 |

Example 10

| Ingredient | Quantity per tablet, mg | % content |
|---|---|---|
| Clarithromycin | 500 | 51 |
| Silicified Microcrystalline cellulose | 220 | 22.5 |
| Maltodextrin M 180 | 220 | 22.5 |
| Glyceryl behenate | 25 | 2.5 |
| Mg Stearate | 10 | 1.0 |
| Hydrophilic Fumed Silica | 5 | 0.5 |
| Tablet weight | 980 | |

Tablets were manufactured by the direct compression method, as described in Example 1. The dissolution profile was determined using the procedure described in Example 1. The results are as follows:

| Time (Hours) | Cumulative % Released |
|---|---|
| 1 | 12 |
| 3 | 43 |
| 5 | 78 |
| 7 | 100 |

Example 11

| Ingredient | Quantity per tablet, mg | % content |
| --- | --- | --- |
| Clarithromycin | 500 | 51 |
| Silicified Microcrystalline cellulose | 220 | 22.5 |
| Maltodextrin M 180 | 220 | 22.5 |
| Glyceryl behenate | 25 | 2.5 |
| Mg Stearate | 10 | 1.0 |
| Hydrophilic Fumed Silica | 5 | 0.5 |
| Tablet weight | 980 | |
| Coating with Opadry YS-1-7006 clear | 29.4 | 3 |

Tablets were manufactured by the direct compression method, in accordance with the procedure described in Example 1. The tablets were coated using perforated pan coating. The dissolution profile was determined using the procedure described in Example 1 and the results are as follows:

| Time (Hours) | Cumulative % Released |
| --- | --- |
| 1 | 10 |
| 3 | 23 |
| 5 | 53 |
| 7 | 75 |

Example 12

| Ingredient | Formulation A Quantity per tablet, mg | Formulation B Quantity per tablet, mg |
| --- | --- | --- |
| Clarithromycin | 500 | 500 |
| Silicified Microcrystalline cellulose | 207.5 | 207.5 |
| Maltodextrin M 180 | 207.5 | 207.5 |
| Glyceryl behenate | 50 | 50 |
| Mg Stearate | 15 | 15 |
| Hydrophilic Fumed Silica | — | 5 |
| Tablet weight | 980 | 985 |

Tablets were manufactured by the direct compression method, as described in Example 1. The dissolution profile was determined using the procedure described in Example 1. The results are as follows:

| Time (Hours) | A Cumulative % Released | B Cumulative % Released |
| --- | --- | --- |
| 1 | 10 | 17 |
| 3 | 20 | 34 |
| 5 | 32 | 49 |
| 7 | 42 | 67 |

Example 13

| Ingredient | Formulation A Quantity per tablet, mg | Formulation B Quantity per tablet, mg |
| --- | --- | --- |
| Clarithromycin | 1000 | 1000 |
| Silicified Microcrystalline cellulose | 33.5 | 45 |
| Citric Acid | 50 | 22 |
| Mg Stearate | 16.5 | 11 |
| PVP K30 | — | 22 |
| Isopropyl alcohol* | — | QS |
| Tablet weight | 1100 | 1100 |

Tablets for formulation A were manufactured by the direct compression method in accordance with the procedure of Example 1.

Tablets for formulation B were manufactured using wet granulation. In the wet granulation method, the drugs and excipients were separately milled using a 40 mesh screen by means of a mechanical vibrosifter. The drugs and excipients were mixed together using a blender at room temperature until homogenous. The milled blender mixture was next mixed using PVP in isopropyl alcohol as the granulating medium to form a wet mass. The wet mass was passed through a 6-12 mesh screen. The milled wet mass was dried at 50-80° C. in a Fluid Bed Dryer. A lubricant which has also been passed through a 6-12 mesh screen is mixed with the dried clarithromycin composition until homogenous and then the resulting mixture is compressed into a tablet using a tablet press.

The release profile for both formulation was determined using the procedure described in Example 3. The results are as follows:

| Time (Hours) | A Cumulative % Released | B Cumulative % Released |
| --- | --- | --- |
| 1 | 100 | 16 |
| 3 | — | 52 |
| 5 | — | 83 |
| 7 | — | 95 |

Example 14

| Ingredient | Formulation A Quantity per tablet mg | Formulation B Quantity per tablet, mg |
| --- | --- | --- |
| Clarithromycin | 1000 | 1000 |
| Silicified Microcrystalline cellulose | 49.12 | 68.8 |
| Maltodextrin M180 | 49.12 | 29.5 |
| Citric Acid | 11.5 | 11.5 |
| Mg Stearate | 17.3 | 17.2 |
| PVP K30 | 23 | 23 |
| Isopropyl alcohol* | QS | QS |
| Tablet weight | 1150 | 1150 |

Tablets were manufactured using the wet granulation method described in Example 13 where isopropyl alcohol was used as the granulating medium. The release profile was determined using the procedure described in Example 3. The results are as follows:

| Time (Hours) | A Cumulative % Released | B Cumulative % Released |
|---|---|---|
| 1 | 10 | 8 |
| 3 | 30 | 27 |
| 5 | 42 | 52 |
| 7 | 63 | 72 |

Example 15

| Ingredient | Macrolide Formulation A Quantity per tablet, mg | Macrolide Formulation B Quantity per tablet, mg |
|---|---|---|
| Clarithromycin | 1000 | 1000 |
| Silicified Microcrystalline cellulose | 29.25 | 16.75 |
| Maltodextrin M180 | 29.25 | 16.75 |
| Glyceryl Behenate | 25 | 50 |
| Mg Stearate | 16.5 | 16.5 |

| Time (Hours) | A Cumulative % Released | B Cumulative % Released |
|---|---|---|
| 1 | 12 | 9 |
| 3 | 26 | 17 |
| 5 | 37 | 23 |
| 7 | 48 | 28 |

The tablets were manufactured using the direct compression method described in Example 1. The dissolution profile was determined using the procedure described in Example 3. The results are as follows:

| Ingredient | Formulation I | Formulation II | Formulation III |
|---|---|---|---|
| Clarithromycin | 500 | 500 | 500 |
| Glyceryl behenate | 25 | 25 | 25 |
| Silicified Microcrystalline Cellulose | 440 | 330 | 210 |
| Maltodextrin | — | 110 | 210 |
| PEG 3350 | 20 | 20 | 20 |
| Magnesium Stearate | 15 | 15 | 15 |
| Ratio: SMCC:Maltodextrin | 100:0 | 75:25 | 50:50 |

The tablets were manufactured by mixing all the ingredients in a suitable blender followed by compression. The dissolution was carried out in pH 5 acetate buffer using USP II apparatus at 50 RPM. The results are as follows:

| | Cumulative % Released | | |
|---|---|---|---|
| Time (Hours) | Formulation I | Formulation II | Formulation III |
| 1 | 58 | 14 | 11 |
| 3 | 85 | 35 | 24 |
| 5 | 93 | 49 | 41 |
| 7 | 93 | 64 | 58 |
| 9 | | | 73 |
| 12 | | | 79 |

The above preferred embodiments and examples were given to illustrate the scope and spirit of the present invention. These embodiments and examples will make apparent to those skilled in the art other embodiments and examples. The other embodiments and examples are within the contemplation of the present invention. Therefore, the present invention should be limited only by the amended claims.

What is claimed is:

1. A controlled release formulation in tablet form comprising a composition comprising a pharmaceutically effective amount of clarithromycin and a lubricating effective amount of a lubricant and a release promoter in a tablet disintegrating effective amounts to facilitate the release of clarithromycin from the tablet and optionally a hydrophobic sustained release agent in the absence of a material selected from the group consisting of alginic acid or salts thereof and hydrophilic sustained release polymers, the composition, comprised of clarithomycin, lubricant, release promoter and, when present in said formulation, hydrophobic sustained release agent, being present in the core of a coated tablet or in an uncoated tablet.

2. The controlled release formulation of claim 1 wherein said composition additionally comprises a binder selected from starch, pregelatinized starch, gelatin, sugar, polyethylene glycol, wax, acacia, tragacanth, acrylic acid and methacrylic acid copolymers, methyl methacrylate copolymers, amino alkyl methacrylate copolymers, polyacrylic acid/polymethacrylic copolymers, polyacrylic acid, and polymethylacrylic acid.

3. The controlled release formulation according to claim 1 wherein clarithromycin is present in a concentration ranging from about 40% by weight to about 99% by weight of the tablet.

4. The controlled release formulation of claim 1 wherein the lubricant is present in amounts ranging from about 1 to about 10% by weight of the tablet.

5. The controlled release formulation according to claim 1 wherein the release promoter is present in amounts ranging from about 0.01% to about 60% by weight of the tablet.

6. The controlled release formulation according to claim 1 wherein the release promoter is hydrophilic.

7. The controlled release formulation according to claim 6 wherein the release promoter is microcrystalline cellulose, solidified microcrystalline cellulose, maltodextrin, starch, or sugar, or combination thereof.

8. The controlled release formulation according to claim 6 wherein the release promoter is present in amounts ranging from about 10% to about 60% by weight of the tablet.

9. The controlled release formulation according to claim 1 wherein the release promoter is a water soluble organic acid.

10. The controlled release formulation of claim 9 wherein the water soluble organic acid is present in amounts ranging from about 0.1% to about 10% by weight of the tablet.

11. The controlled release formulation according to claim 9 wherein the water soluble organic acid is citric acid, benzoic acid, tartaric acid or cinnamic acid.

12. The controlled release formulation according to claim 1 wherein the release promoter is a hydrophilic surfactant.

13. The controlled release formulation according to claim 12 wherein the hydrophilic surfactant is a non-ionic surfactant or ionic surfactant.

14. The controlled release formulation according to claim 13 wherein the hydrophilic surfactant is sodium lauryl sulfate.

15. The controlled release formulation according to claim 2 wherein the binder is a hydrophilic polymer.

16. The controlled release formulation according to claim 15 wherein the hydrophilic polymer is polyethylene glycol.

17. The controlled release formulation according to claim 15, wherein the polymeric binder is present in amounts ranging from about 0.1 to about 10% by weight of the tablet.

18. The controlled release formulation according to claim 1 wherein microcrystalline cellulose is additionally present.

19. The controlled release formulation according to claim 1 wherein maltodextrin is additionally present.

20. The controlled release formulation according to claim 1 wherein the tablet additionally comprises maltodextrin in combination with a cellulose derivative selected from the group consisting of microcrystalline cellulose and solidified microcrystalline cellulose.

21. The controlled release formulation according to claim 1 which additionally comprises a water insoluble pharmaceutically acceptable non-polymeric material.

22. The controlled release formulation according to claim 21 wherein the non-polymeric material is a wax.

23. The controlled release formulation according to claim 1 tablet is coated with a water soluble polymer or water insoluble polymer or combination thereof.

24. The controlled release formulation according to claim 23 wherein the coating is present in amounts ranging from about 0.5% to about 10% of the tablet.

25. A method for preparing a sustained release formulation comprised of clarithromycin in tablet form which method comprises milling a composition comprised of a therapeutically effective amount of clarithromycin and a lubricating effective amount of a lubricant, and optionally a release promoter in tablet disintegrating effective amounts to facilitate the release of clarithromycin from the tablet and optionally a hydrophobic sustained release agent, mixing said milled composition and compressing the mixture into a tablet, wherein said composition is present in an uncoated tablet or in the core of a coated tablet, the formulation being free of a material selected from the group consisting of alginic acid or salts thereof and hydrophilic sustained release polymers.

26. The method according to claim 25 wherein the tablet additionally comprises a binder selected from the group consisting of starch, gelatin, sugar, polyethylene glycol, wax, acacia, tragacanth, acrylic acid and methacrylic acid copolymers, methyl methacrylate copolymers, amino alkyl methacrylate copolymers, polyacrylic acid/polymethacrylic copolymers, polyacrylic acid, and polymethylacrylic acid.

27. The method according to claim 25 wherein clarithromycin is present in a concentration ranging from about 40% by weight to about 99% by weight of the tablet.

28. The method according to claim 25 wherein the lubricant is present in amounts ranging from about 1 to about 10% by weight of the tablet.

29. The method according to claim 25 wherein the release promoter is present in amounts ranging from about 0.01% to about 60% by weight of the tablet.

30. The method according to claim 25 wherein the release promoter is hydrophilic.

31. The method according to claim 30 wherein the release promoter is microcrystalline cellulose, silicified microcrystalline cellulose, maltodextrin, starch, sugar, or combination thereof.

32. The method according to claim 29 wherein the release promoter is present in amounts ranging from 10% to about 60% by weight of the tablet.

33. The method according to claim 25 wherein the release promoter is a water soluble organic acid.

34. The method according to claim 33 wherein the water soluble organic acid is present in amounts ranging from about 0.1% to about 10% by weight of the tablet.

35. The method according to claim 33 wherein the water soluble organic acid is citric acid, benzoic acid, tartaric acid or cinnamic acid.

36. The method according to claim 25 wherein the release promoter is a hydrophilic surfactant.

37. The method according to claim 36 wherein the hydrophilic surfactant is a non-ionic surfactant or ionic surfactant.

38. The method according to claim 37 wherein the hydrophilic surfactant is sodium lauryl sulfate.

39. The method according to claim 26 wherein the binder is a hydrophilic polymer.

40. The method according to claim 39 wherein the hydrophilic binder is polyethylene glycol.

41. The method according to claim 39 wherein the polymeric binder is present in amounts ranging from about 0.1 to about 10% by weight of the tablet.

42. The method according to claim 25 wherein the tablet is coated with a water soluble polymer or water insoluble polymer.

43. The method according to claim 25 wherein the mixture is effected in the presence of a granulating solvent and the resulting mixture is subjected to wet granulation and the solvent is removed therefrom prior to compressing the mixture into a tablet.

44. The controlled release formulation of claim 1 wherein the clarithromycin is present in amounts greater than about 75% by weight of the tablet.

45. The method according to claim 25 wherein the clarithromycin is present in amounts greater than about 75% by weight of the tablet.

46. The method according to claim 7 wherein the release promoter is lactose.

47. The controlled release formulation according to claim 31 wherein the release promoter is lactose.

* * * * *

UNITED STATES PATENT AND TRADEMARK OFFICE
CERTIFICATE OF CORRECTION

| | | |
|---|---|---|
| PATENT NO. | : 8,507,000 B2 | Page 1 of 1 |
| APPLICATION NO. | : 10/555849 | |
| DATED | : August 13, 2013 | |
| INVENTOR(S) | : Nirmal Mulye | |

It is certified that error appears in the above-identified patent and that said Letters Patent is hereby corrected as shown below:

On the Title Page

It Should Read:

Item (56)    References Cited

U.S. PATENT DOCUMENTS 3,931,404     A    1/1976 Fülberth et al.
4,588,712     A    5/1986 Toscano
5,141,926     A    8/1992 Weber et al.
5,605,889     A *  2/1997 Curatolo et al. ............ 514/29
5,705,190     A    1/1998 Broad et al.
6,010,718     A *  1/2000 Al-Razzak et al. ........ 424/464
6,068,859     A *  5/2000 Curatolo et al. .......... 424/490
6,248,363     B1*  6/2001 Patel et al. ................. 424/497
6,642,276     B2* 11/2003 Wadhwa .................. 514/781
6,673,369     B2*  1/2004 Rampal et al. ............. 424/468
2002/0136766 A1  9/2002 Rudnic et al.
2003/0077324 A1  4/2003 Mulye Signed and Sealed this
Thirtieth Day of September, 2014

Michelle K. Lee
*Deputy Director of the United States Patent and Trademark Office*